United States Patent [19]

Stensaas

[11] Patent Number: 4,662,884
[45] Date of Patent: May 5, 1987

[54] PROSTHESES AND METHODS FOR PROMOTING NERVE REGENERATION

[75] Inventor: Larry J. Stensaas; R. Joseph Todd, both of Salt Lake City, Utah; Philip M. Triolo, Enschede, Holland

[73] Assignee: University of Utah Research Foundation, Salt Lake City, Utah

[21] Appl. No.: 603,835

[22] Filed: Apr. 25, 1984

[51] Int. Cl.⁴ .............................................. A61F 2/04
[52] U.S. Cl. ........................................ 623/12; 623/66; 128/1 R; 128/334 R; 128/335.5
[58] Field of Search ................... 623/66, 12; 128/1 R, 128/334 R, 334 C, 335.5, 155

[56] References Cited

U.S. PATENT DOCUMENTS

| | | |
|---|---|---|
| 397,861 | 2/1889 | Kelly . |
| 783,031 | 2/1905 | Fell . |
| 947,146 | 1/1910 | Von Bolton . |
| 1,151,300 | 8/1915 | Soresi . |
| 1,217,637 | 2/1917 | Rink . |
| 1,308,799 | 7/1919 | Masland . |
| 1,329,121 | 1/1920 | Hachman . |
| 1,470,707 | 10/1923 | Bates . |
| 1,983,601 | 12/1934 | Conn ................................. 128/304 |
| 2,015,509 | 9/1935 | Austin ................................ 148/16 |
| 2,071,250 | 2/1937 | Carothers ........................... 260/106 |
| 2,127,903 | 8/1938 | Bowen ................................ 128/334 |
| 2,332,826 | 10/1943 | Fryer et al. ....................... 113/116 |
| 2,451,703 | 10/1948 | Weiss ................................. 128/334 |
| 2,453,056 | 11/1948 | Zack ................................... 128/334 |
| 2,514,665 | 7/1950 | Myller ................................ 128/2 |
| 2,737,402 | 3/1956 | Frumerie et al. ................... 285/22 |
| 2,764,683 | 9/1956 | Paust et al. ........................ 250/36 |
| 3,048,177 | 8/1962 | Takaro ................................ 128/334 |
| 3,155,095 | 11/1964 | Brown ................................. 128/334 |
| 3,157,181 | 11/1964 | McCarthy ............................ 128/404 |
| 3,221,746 | 12/1965 | Noble ................................. 128/334 |
| 3,254,650 | 6/1966 | Collito ................................ 128/334 |
| 3,272,204 | 9/1966 | Artandi et al. ..................... 128/334 |
| 3,317,924 | 5/1967 | Le Veen .............................. 3/1 |
| 3,320,947 | 5/1967 | Knoll .................................. 128/2.1 |
| 3,357,432 | 12/1967 | Sparks ................................ 128/334 |
| 3,387,608 | 6/1968 | Figar .................................. 128/2.06 |
| 3,405,715 | 10/1968 | Hagfors ............................... 128/418 |
| 3,479,670 | 11/1969 | Medell ................................ 3/1 |
| 3,561,448 | 2/1971 | Peternel ............................. 128/334 |
| 3,626,926 | 12/1971 | Kuzin et al. ........................ 128/1 C |
| 3,648,295 | 3/1972 | Palma ................................. 3/1 |
| 3,677,243 | 7/1972 | Nerz ................................... 128/214.4 |
| 3,718,134 | 2/1973 | Brindley ............................. 128/2.1 |
| 3,724,467 | 4/1973 | Avery et al. ........................ 128/418 |
| 3,786,817 | 1/1974 | Palma ................................. 128/334 |
| 3,805,793 | 4/1974 | Wright ................................ 128/334 |
| 3,822,708 | 7/1974 | Zilber ................................. 128/419 |
| 3,833,002 | 9/1974 | Palma ................................. 128/334 |
| 3,841,305 | 10/1974 | Hallgren ............................. 128/1.3 |
| 3,841,306 | 10/1974 | Hallgren ............................. 128/1.5 |

(List continued on next page.)

OTHER PUBLICATIONS

Alix Freedman, "Nerve Regeneration Seen in Procedure Using Protein Tube," Wall Street Journal, p. 23 (Nov. 5, 1986, Western Edition).

Joseph M. Rosen et al., "Fascicular Tubulization: A Cellular Approach to Peripheral Nerve Repair," Annals of Plastic Surgery, vol. II, No. 5 (Nov. 1983).

Brooke Rutledge Seckel et al., "Nerve Regeneration Through Synthetic Biodegradable Nerve Guides: Reg-

(List continued on next page.)

Primary Examiner—Richard J. Apley
Assistant Examiner—Alan W. Cannon
Attorney, Agent, or Firm—Workman, Nydegger & Jensen

[57] ABSTRACT

The present invention is directed to prostheses and methods for promoting nerve regeneration. The proximal and distal ends of a severed nerve are brought into close proximity and are enclosed by a tubular prosthesis. In one preferred embodiment, a monosuture is used to hold the nerve ends in close proximity. A tight seal is formed between the prosthesis and the injured nerve so as to isolate the injured nerve within the prosthesis from the rest of the body of the host. Additionally, in one preferred embodiment, nerve grafts may be incorporated into the prosthesis and nerve regeneration promoting substances may be incorporated within the nerve graft to further enhance nerve regeneration. Prostheses and methods for inhibiting the formation of neuromas are also disclosed.

27 Claims, 5 Drawing Figures

U.S. PATENT DOCUMENTS

| | | |
|---|---|---|
| 3,883,901 | 5/1975 | Coquard et al. .......................... 3/1 |
| 3,896,817 | 7/1975 | Hursen et al. ...................... 128/419 |
| 3,915,151 | 10/1975 | Kraus .................................. 128/1.5 |
| 3,916,905 | 11/1975 | Kuhn .............................. 128/334 R |
| 3,918,459 | 11/1975 | Horn ................................. 128/419 |
| 3,938,528 | 2/1976 | Bucalo ............................. 128/334 |
| 3,955,560 | 5/1976 | Stein et al. ......................... 128/2.1 |
| 3,960,151 | 6/1976 | Kuhn ................................ 128/334 |
| 3,974,835 | 8/1976 | Hardy, Jr. ......................... 128/334 |
| 4,019,518 | 4/1977 | Maurer et al. ................... 128/419 |
| 4,019,519 | 4/1977 | Geerling .......................... 128/422 |
| 4,026,300 | 5/1977 | DeLuca et al. .................... 128/418 |
| 4,052,978 | 10/1977 | Eugenio ......................... 128/2.1 C |
| 4,056,097 | 11/1977 | Maass ................................ 128/1.5 |
| 4,057,069 | 11/1977 | Dorffer et al. .................... 128/421 |
| 4,141,365 | 2/1979 | Fischell et al. ................... 128/404 |
| 4,157,087 | 6/1979 | Miller et al. ..................... 128/741 |
| 4,245,638 | 1/1981 | Lebeck et al. .................... 128/334 |
| 4,267,842 | 5/1981 | Archibald ........................ 128/334 |
| 4,279,256 | 7/1981 | Bucalo .............................. 128/419 |
| 4,306,561 | 12/1981 | de Medinaceli .............. 128/303.13 |
| 4,331,150 | 5/1982 | Braun et al. ...................... 128/334 |
| 4,331,157 | 5/1982 | Keller, Jr. et al. ................. 128/419 |
| 4,379,665 | 4/1983 | Hendershot et al. ............. 408/204 |
| 4,458,678 | 7/1984 | Yanaas et al. .................... 128/155 |
| 4,534,349 | 8/1985 | Barrows ...................... 128/334 R |

OTHER PUBLICATIONS ulation by the Target Organ," Plastic and Reconstructive Surgery, vol. 74, No. 2 (Aug. 1984).

B. Uzman et al., "Mouse Sciatic Nerve Regeneration Through Semipermeable Tubes: A Quantitative Model," 9 Journal of Neuroscience Research, 325–338 (Apr. 1983).

F. Longo et al., "Neuronotrophic Activities Accumulate In Vivo Within Silicone Nerve Regeneration Chambers," 261 Brain Research, 109–117 (Feb. 1983).

G. Lundborg et al., "Nerve Regeneration Model and Trophic Factors in Vivo," 232 Brain Research, 157–161 (1982).

G. Lundborg et al., "Nerve Regeneration in Silicone Chambers: Influence of Gap Length and of Distal Stump Components," 76 Experimental Neurology, 361–375 (1982).

G. Lundborg et al., "In Vivo Regeneration of Cut Nerves Encased in Silicone Tubes," 41 Journal of Neuropathlogy and Experimental Neurology, 412–422, No. 4 (1982).

H. Molander et al., "Regeneration of Peripheral Nerve Through a Polyglactin Tube," 5 Muscle and Nerve, 54–57 (1982).

J. Rosen et al., "Suture and Sutureless Methods of Repairing Experimental Nerve Injuries," Chapter 25 of Nerve Repair and Regeneration; Its Clinical and Experimental Basis (D. L. Jewett and H. R. McCarroll, eds.) (1979).

Sir Sydney Sunderland, "Nerves and Nerve Injuries," Chapters 1, 2, 46, 48, and 49 (pp. 3–60, 533–550, and 569–602), 2d ed., published by Churchill Livingstone (1978).

Alan Peters et al., "The Fine Structure of the Nervous System: The Neurons and Supporting Cells," Chapters 6 and 12 (pp. 181–230 and 323–331), 2d ed., published by the W. B. Saunders Co. (1976).

"Silastic Nerve Cuff," advertising bulletin of Dow Corning Corporation, Midland, MI, Bulletin 51–046A (Jan. 1974).

T. Ducker et al., "Peripheral Nerve Injuries: A Comparative Study of the Anatomical and Functional Results Following Primary Nerve Repair in Chimpanzees," 133 Milit. Med., 298–302 (1968).

P. Weiss, "Sutureless Reunion of Severed Nerves with Elastic Cuffs of Tantulum," 1 J. Neurosurg., 219–225 (1944).

"Nerve Tube Implant," (source unknown).

W. Kuhn et al., "A Nerve Implant Prosthesis for Facilitating Peripheral Nerve Regeneration," (unknown whether this reference has ever been published).

PROSTHESES AND METHODS FOR PROMOTING NERVE REGENERATION

BACKGROUND

1. Field of the Invention

The present invention relates to nerve prostheses and the repair of injured nerve tissue. In particular, the present invention is directed to prostheses and methods for promoting nerve regeneration and for inhibiting the formation of neuromas in traumatized nerve tissue.

2. The Prior Art

Nerve are vital to the basic operation and function of the human body. Injury to a nerve can result in a partial or total loss of the sensation, control, or use of a member or portion of the body. Although methods currently exist for surgically repairing nerve tissue, such methods are not always possible and are commonly not completely successful in achieving a restoration of sensation, control, and use of the affected portion of the body.

One method of repair involves the use of very fine sutures (nultiple microsutures) to sew the severed nerve ends together. Such mircosurgical procedures are typically conducted with the use of a microscope, and are extremely tedious and time consuming. Additionally, such microsurgical procedures are often not successful, particularly in view of the large amount of time which typically transpires before surgery can be completed, as well as in view of the amount of manipulation which is required while the ends of the injured nerve are being sewn together using these microsurgical techniques.

Where substantial nerve injury has occurred, it is often physically impossible to suture the severed nerve ends together. Thus, for more major nerve injuries, nerve grafts are often used as a nerve replacement. However, these nerve grafts suffer from many drawbacks. First, the chances for success in achieving nerve regeneration using such grafts has been extremely unpredictable. Second, there is the potential for an autoimmune response by the body to the nerve graft.

Not only has the prior art failed to provide reliable prostheses and methods for regenerating nerve tissue, but the prostheses and methods used by the proir art often result in an extremely undesirable and painful condition referred to in the art as a "neuroma." Simply stated, a neuroma consists of a mass of nerve fibers growing irregularly from the injured proximal nerve end. This condition can be so painful, that is has driven some patients to suicide. Unfortunately, there are no consistently effective methods known in the prior art for inhibiting the formation of neuromas.

It would, therefore, be a signficant advancement in the art to provide effective prostheses and methods for promoting regeneration of nerve tissue. It would also be an advancement in the art to provide such prostheses which could be implanted in a patient without tedious and time-consuming installation techniques.

It would be still a further advancement in the art if the prostheses could incorporate a nerve graft which is not rejected by the body. It would be yet another significant advancement in the art to provide a method for inhibiting and substantially preventing the formation of neuromas. Such prostheses and methods are disclosed and claimed herein.

BRIEF SUMMARY AND OBJECTS OF THE INVENTION

The present invention provides nerve prostheses and methods for promoting nerve regeneration in a variety of different situations. In each situation, a tubular prosthesis which is made of biocomatible material and which is impermeable to fluids associated with the injured nerve is used to promote regeneration of the injured nerve.

A first application of the present invention is where there is no gap (or a very short gap) between the injured nerve ends. Using an endoneuril monosuture, the proximal and distal ends of the severed nerve are brought together and held into close proximity to each other, preferably within at least about 0.5 millimeters. Next, the proximal end of the severed nerve and the distal end of the severed nerve are enclosed within the tubular prosthesis. The prosthesis is firmly secured to the nerve, particularly, around the proximal end of the nerve by the resilient properties of the tubular prosthesis, so as to seal the severed nerve ends from the environment outside of the prosthesis. In order to achieve a firm seal between the prosthesis and the nerve, it has been found that a portion of the epineural connective tissue from the area around the severed nerve ends may optionally be removed.

Thus,, the tubular prostheses and methods of the present invention serve (1) to maintain the proximal and distal nerve ends in close proximity without using the prior art procedure of suturing the very ends of the nerve together, and (2) to isolate the nerve ends from the environment outside of the prosthesis.

A second application of the present invention is where more substantial injury to the nerve has occurred, i.e., where there is a gap of about 1-2 centimeters or more between the severed nerve ends after the nerve ends have been coapted using a monosuture. In this situation, it may be preferable to use an animal nerve graft in conjunction with the tubular prosthesis of the present invention. According to the present invention, a nerve graft is prepared so as to minimize the potential for rejection of the nerve graft by the body, and the nerve graft is positioned within the tubular prosthesis. The proximal and distal ends of the severed nerve are enclosed within the tubular prosthesis as discussed above.

In this second application of the present invention, however, the proximal end of the severed nerve is positioned in close proximity to one end of the nerve graft within the tubular prosthesis, i.e., within at least about 0.5 millimeters, while the distal end of the severed nerve is similarly positioned and held within close proximity to the other end of the nerve graft within the prosthesis.

In some instances, it may be desirable to impregnate the animal nerve graft with nerve regeneration promoting substances or components to further promote regeneration of the injured nerve. Nerve regeneration promoting substances such as fibronectin, angiogenesis factors, nerve growth factor, extracts of central nervous tissue, and Schwann cells may be used for this purpose.

It is, therefore, an object of the present invention to provide effective prostheses and methods for promoting nerve regeneration in a variety of different types of nerve injury.

Another object of the present invention is to provide nerve prostheses which are quickly and easily implanted into a patient.

A further object of the present invention is to provide nerve prostheses which may incorporate a nerve graft that has been treated in order to minimize the potential for rejection of the graft by the body.

A still further object of the present invention is to provide a method for inhibiting and substantially preventing the formation of neuromas in injured nerve tissue.

These and other objects and features of the present invention will become more fully apparent from the following description and appended claims, taken in conjunction with the accompanying drawings.

DETAILED DESCRIPTION OF THE PREFERRED EMBODIMENTS

A. General Discussion of Nerve Structure and the Principles of Nerve Regeneration The following general discussion relating to nerve structure and the regeneration of nerve tissue is given so that the particular problems which have been solved by the present invention may be better understood. It should be noted that while some of the following discussion is based upon facts and principles which are known in the art, much of the following discussion is based upon particular discoveries made by the inventor which have not heretofore been known and understood, and which are important in solving the problems which are addressed by the present invention.

Moreover, it will be understood that a few portions of the following discussion are based upon theory which has been formulated to explain the phenomenon of nerve regeneration. This information is given so as to fully enable one of ordinary skill in the art to understand the operation of and the importance of the novel features of the present invention in promoting the regeneration of nerve tissue and in inhibiting or substantially preventing the formation of neuromas. Nevertheless, it will be appreciated that while sucn theory aids in understanding the present invention, the effectiveness and utility of the present invention does not necessarily depend upon the absolute accuracy of such scientific theory.

The structure of a typical nerve is quite complex. With a single nerve is a plurality of "fasciculi" or "funiculi" interconnected by connective tissue known as the epineurium. The epineurium consists mainly of dense collagen, blood vessels, and fibroblasts.

Each funiculus within the nerve actual contains a multitude of nerve fibers or "axons"; hence, a funiculus is often referred to as a "nerve bundle." Typically, each funiculus comprises the following elements: (1) a perineurium, (2) nerve fibers or axons, (3) Schwann cells (with or without a myelin sheath), (4) blood vessels, (5) fibroblasts, and (6) endoneurial fluid.

The perineurium is a laer of cells around each nerve bundle or funiculus. The tissue within the perineurium surrounding the individual nerve fibers of a funiculus is what is referred to as the endoneurium. Endoneurial fluid flows through the endoneurium within funiculi.

The perineurium acts as an impermeable barrier to keep foreign substances out of the funiculus and to keep endoneurial fluid contained within the funiculus. Thus, the perineurium serves to retain a fluid environment which is favorable to the axons and Schwann cells within the funiculus. The myelin sheath, which is found around many axons and which acts as an insulator for the axons, is made by the Schwann cells which are positioned around the axon. The elongated Schwann cells are enclosed in an outer, tubular basal lamina or endoneurial tube. The Schwann cells also serve to form a protoplasmic sheath for unmyelinated nerve fibers.

Inside of the perineurium of each funiculus are found trophic substances which stimulate, inter alia, (1) the growth of blood vessels, (2) the fibroblasts to make collagen, (3) the growth of the axons, and (4) the maintenance of the nerve cell bodies. These trophic substances are produced by the Schwann cells and are found only in the endoneurial compartment of each funiculus; these trophic substances are not outside of the funiculus in the epineurial region of the nerve.

Nerve impulses pass down the membrane of each axon by utilizing discontinuities in the Schwann cells and in the myelin sheath of myelinated axons; these discontinuities are known as "nodes of Ranvier." The nerve impulse hops from one node of Ranvier to the next node of Ranvier down the axon. The presence of myelin serves to speed up the propagation of the nerve pulse.

When a nerve is injured, the Schwann cells attack the damaged and degeneating nerve tissue so as to degrade the nerve tissue into components which can be removed through the blood capillaries. During this time, the Schwann cells begin to divide and accelerate their production of the trophic substantes. Also during this time, the Schwann cells: (1) stimulate the growth of the regenerating nerve fibers or axon sprouts arising from the individual nerve fibers, (2) stimulate the proliferation of fibroblasts which are capable of producing collagen, (3) stimulate the blood vessels to grow, and (4) stimuate the regeneration of the injured perineurium. As can be seen, the Schwann cells play an important role in the regeneration of the nerve tissue which has been subjected to severe trauma or injury.

Upon injury to a nerve, many events transpire other than activation and proliferation of the Schwann cells. For example, each myelinated axon of the severed nerve divides into a multiplicity of fine regenerating nerve fibers or axon sprouts, which sprouts are frequently enclosed within a small perineurial sheath. The group is regenerating nerve sprouts enclosed within the new perineurial sheath and the Schwann cells associated with each regenerating nerve sprout of the axon, are collectively referred to as a "regenerating unit." In the regeneration of a nerve, the regenerating units only grow out from the proximal end of the severed nerve; this growth is directed towards the distal end of the severed nerve.

These regenerating units continue to grow and extend across the gap between the proximal and distal ends of the severed nerve. The small perineurial sheaths disappear as the regenerating units bridge the gap, and the regenerating sprouts continue down the distal end of the severed nerve and are eventually guided by Schwann cells to muscle or sensory sites.

Bridging of the gap by the regenerating units is necessary in order for there to be successful regeneration of the nerve. After the gap is bridged by the regenerating units, the individual perineurial sheaths around the nerve fibers of the myelinated axon of each regenerating unit disappear, and a single perineurial sheat forms around the regenerated funiculus.

When the nerve is first severed, cytoplasm oozes from the transected axons of the severed nerve, and the transected axons die back to a node of Ranvier. Subsequently, the regenerating units begin to develop; these regenerating units grow and extend out of the proximal end of the severed nerve towards the distal end thereof.

In order for a regenerating unit to bridge the gap, it is essential that there be a sufficient quantity of Schwann cells present in the area of the gap. When the axons of the regenerating units finally meet Schwann cells in the distal end of the severed nerve, the production of Schwann cells, perineurial cells, and collagen ceases, but the axons continue to grow along the channel formed by the elongated Schwann cells and the endoneurial tubes.

If regenerating units do not grow towards the distal end of the severed nerve, a neuroma may result. A neuroma is the collective result of the misdirected growth of many regenerating units. In a neuroma, growth of the regenerating units generally occurs in a random fashion in directions substantially away from the distal end of the severed nerve. In fact, frequently, the regeneration units of a neuroma will grow within the epineurium of the proximal nerve end in a direction substantially opposite of the distal nerve end.

One reason that neuromas form in the area of injured nerve tissue is that the growing regenerating units, which begin to extend from the proximal end of the severed nerve, emit trophic or growth stimulating substances which are necessary for nerve regeneration. These substances escape from the open, growing ends of the regenerating units, diffusing in all directions, thus encouraging unregulated development of fibroblasts and capillaries in many different directions and leading to growth of the regenerating units in many differet directions. In this regard, the endoneurial fluid flowing down the nerve acts as a carrier for the trophic substances and casues them to be emitted from the ends of the regenerating units.

Since the fibroblasts surrounding the regenerating units synthesize collagen in the presence of trophic substances, a neuroma is typically characterized by the progressive formation of a dense collagen matrix. As the dense collagen builds up, it eventually binds the regenerating units, and may cause pain upon mechanical deformation or stimulation of the regenerated axons.

Thus, it will be appreciated that one of the important principles of the present invention is promoting regeneration of nerve tissue is the discovery that the regenerating units are preferably directed in a straight path toward the distal end of the severed nerve. As will be discussed in more detail hereinafter, one of the key features of the prostheses within the scope of the present invention is that they both orient and "pave the road" for the regenerating units by promoting oriented growth of the fibroblasts and the capillaries. This enables the regenerating units to more easily find the distal end of the severed nerve, thereby minimizing the possibility that a neuroma will be formed. Moreover, as discussed hereinafter, the present invention also provides for directing the trophic substances in a path between the proximal and distal ends of the severed nerve, and for avoiding the escape of these trophic substances to other areas surrounding the severed nerve.

B. Presently Preferred Embodiments of the Present Invention

Figure 1:
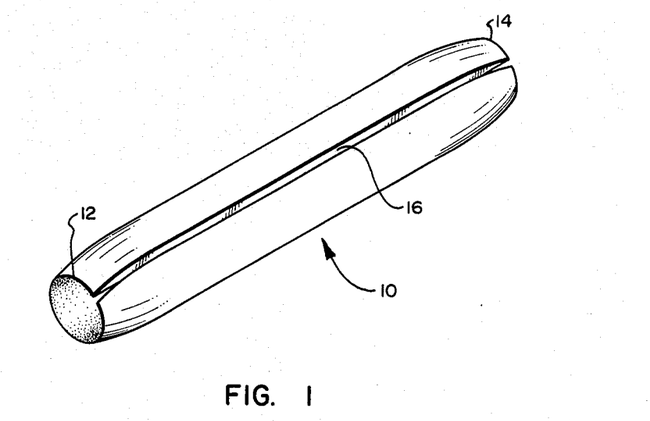
FIG. 1 is a perspective view of a preferred embodiment of a tubular prosthesis within the scope of the present invention.

Reference is now made to the drawings wherein like parts are designated with like numerals throughout. Referring now to FIG. 1, a tubular nerve prosthesis made in accordance with the present invention is generally designated 10. Nerve prosthesis 10 preferably has a generally constant inner diameter; the nerve prosthesis may also be configured with rounded or tapered ends 12 and 14 which are formed by gradually decreasing the thickness of the wall of tubular prosthesis 10 at its respective ends It has been found that by employing rounded or tapered ends in a prosthesis made in accordance with the present invention, movement of the nerve with respect to the prosthesis is minimized, yet the outer surface of the prosthesis is still allowed to move with respect to other nearby structures.

Importantly, never prosthesis 10 is made of a layer of a resilient, yet renitent, biocompatible material which is impermeable to fluids associated with nerve tissue. Such resiliency and renitency may be provided, for example, by using a relatively thick layer of a flexible biocompatible material. Additionally, it has been found presently preferable to construct the nerve prosthesis from a material which is transparent so as to enable a surgeon employing the prostheses to see the position of the injured nerve within the prosthesis when used in accordance with the present invention.

For example, materials such as silicone (e.g., silicone rubber), polyurethane, Teflon (Teflon is a trademark of the DuPont Corporation), and nitrocellulose have been found to be suitable for these purposes of the present invention. Silicone rubber is presently the most preferred material for the prostheses of the presention invention, since it is elastic and has been found not to adhere to the surrounding connective tissue. As will be readily appreciated, it is desirable to minimize the adherence of the prosthesis to the surrounding connective tissue. However, it will be understood that the foregoing materials are given by way of example only, and that other materials may be suitable for forming nerve prostheses in accordance with the present invention.

For purposes of the present invention, it is very important that nerve prosthesis 10 be fabricated of a material which is substantially impermeable to fluids associated with nerve tissue. In particular, it is important that prosthesis 10 be constructed of a material which will not allow escape of substantial amounts of the trophic substances and fluids from the interior of the prosthesis to the exterior of the prosthesis. Such impermeability keeps the trophic substances within the tubular prosthesis so as to encourage nerve regeneration in a direct path from the proximal end to the distal end of the severed nerve.

It is also important that the wall of prosthesis 10 be of sufficient resiliency and renitency so that it will close around the injured nerve ends and form a tight seal around the injured nerve. It has been found that by constructing the wall with a thickness of about 30%-50% of the inner diameter of prosthesis 10, sufficient resiliency and renitency are obtained for this purpose where prosthesis 10 is made of silicone rubber. This percentage range may of course decrease somewhat with more strongly elastic materials. Table I, which follows, provides examples of prostheses within the scope of the present invention, correlating exemplary values for the diameter and tubular wall thickness of various prostheses made of silicone rubber:

TABLE I

| Wall Thickness of Prosthesis (mm) | Inner Diameter of Prosthesis (mm) |
| --- | --- |
| 0.5 | 1.0 |
| 0.65 | 1.5 |
| 0.75 | 2.0 |
| 1.0 | 2.5 |

Although the wall of each prosthesis made in accordance with the present invention should be of sufficient thickness to supply the resiliency and renitency needed to allow the prosthesis to close around the injured nerve ends and form a tight, internal pressure-resistant seal, at the same time, it is desirable to minimize the size of the prosthesis so that it can be easily accommodated within the tissue of the host. Hence, it is presently preferably to construct the prosthesis with a wall having sufficient thickness to provide for the resiliency needed in order to form a firm seal, yet thin enough that the prosthesis can be easily accommodated within the host.

It will be appreciated that the minimum wall thickness which will be necessary in order to provide the required resiliency and renitency will vary from the material to material. By selecting a material which is resilient and renitent in relatively small thicknesses, a prosthesis may be provided with both provides the required resiliency and renitency, yet optimizes the accommodaion of the prosthesis within the host.

The exemplary wall thicknesses set forth hereinabove, i.e., about 30%-50% of the inner diameter of the prosthesis, is the range of wall thicknesses which have been found to produce these results when the prosthesis is made of silicone rubber. Similarly, the exemplary wall thicknesses given in Table I above are also for silicone rubber. It will be appreciated that other materials may be more resilient and renitent than silicone rubber at smaller thicknesses, and that thus, the thickness ranges and examples set forth hereinabove with respect to silicone rubber are given by way of example only and should not be considered restrictive. Indeed, by using materials such as polyurethane to form a prosthesis in accordance with the present invention, wall thicknesses significantly smaller than those characteristic of silicone rubber may be used to provide the resiliency and renitency needed to form a firm seal in accordance with the present invention.

Tubular nerve prosthesis 10 is also preferably provided with a longitudinal slit 16 which extends along the entire length of the tubular prothesis. Slit 16 allows for the longitudinal opening of prosthesis 10 so as to permit insertion of the ends of the severed nerve into the prosthesis.

Importantly, prothesis 10 is made of a resilient, yet renitent, material and has an inner diameter corresponding roughly to the outer diameter of the injured nerve. The resilient nature of prosthesis 10 helps the prosthesis to close to form a firm seal around the severed nerve when the severed nerve ends are inserted into the prosthesis and the pressure applied to open the prosthesis at slit 16 is released. Because of the renitent nature of the prosthesis, the prosthesis will resist internal pressures from within, thereby serving to prevent such internal pressures from causing the prosthesis to open along slit 16.

Hence, it will be appreciated that although a gap is shown along slit 16 in FIG. 1 for purposes of illustration, the walls of prosthesis 10 close to form a relatively tight seal along slit 16. Thus, in the closed position, nerve prosthesis 10 functions as though it has a continuous tubular surface with no slit.

Prosthesis 10 is thus self-closing in that the thick wall of resilient, yet renitent, material restores itself such that fluids associated with the nerve will not generally be capable of escaping from prosthesis 10. In this manner, a tight seal is provided along slit 16 so that prosthesis 10 acts as a continuous device. Hence, it will be appreciated that slit 16 serves to accommodate insertion of a severed nerve funiculus into the prosthesis 10, and is subsequently sealed off after insertion by the action of the walls of the prosthesis so as to maintain the tight seal which is of importance in the present invention.

The tightly fitting prosthesis of the present invention provides a straight path for the regenerating units extending out of the proximal end of the severed nerve, so that they may more easily find the distal end of the severed nerve. Hence, the tightly fitting prosthesis minimizes the chances of the regenerating axons being misrouted, thereby minimizing the chances of the formation of a neuroma.

Additionally, the tightly fitting and impermeable prosthesis of the present invention maintains the trophic substances with a tubular pathway so as to encourage axon growth within the prosthesis, while substantially discouraging axon growth in any other direction. Hence, the tubular prostheses of the present invention provide for proper orientation of the regenerating units, and channels the trophic substances necessary for nerve regeneration in the proper direction.

Although there may be many different methods for fabricating a prosthesis in accordance with the present invention, one presently preferred example of a procedure for manufacturing a nerve prosthesis within the scope of the present invention is given in Example 1 below.

EXAMPLE 1

A presently preferred method for making a nerve prosthesis within the scope of the present invention involves the injection of liquid silicone rubber into a mold configured so as to form a prosthesis substantially similar to that illustrated in FIG. 1.

It has been found desirable to configure the mold so that the outer surface of the prosthesis is smooth, while the inner surface of the prosthesis is somewhat rough or textured. The smooth outer surface allows the prosthesis to slip with respect to the adjacent connective tissue, and the rough inner surface of the prosthesis provides for better adherence of the prosthesis to the nerve ends after the prosthesis is positioned. The prosthesis is then slit longitudinally to provide a prosthesis substantially similar in configuration to the prosthesis shown in FIG. 1.

Figure 2:
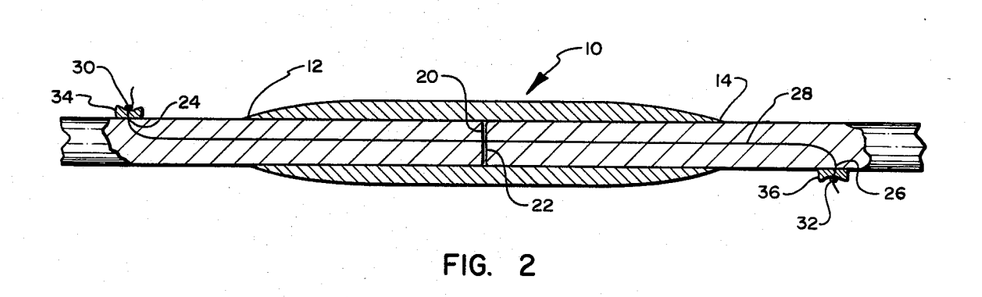
FIG. 2 is a longitudinal cut-away, cross-sectional view of the embodiment of the tubular prosthesis of FIG. 1 as used to treat a nerve injury where there is only a very small gap (or no gap) between the injured nerve ends.

Referring now to FIG. 2, the application of the nerve prosthesis of the present invention to a first type of nerve injury is illustrated. One of the most common types of nerve injury involves the situation where the nerve has been severed so that there is only a very small gap (or no gap) between the ends of severed nerve. In this situation, the tubular nerve prosthesis 10 is used to bring the proximal end 20 and the distal end 22 of the severed nerve into close proximity in the following manner.

Preferably, a fascicular monosuture 28 is first used to coapt severed nerve ends 20 and 22 before the nerve prosthesis is placed around the severed nerve ends. This monosuture 28 is formed by introducing a long needle carrying a very fine suture thread through site 26 of the perineurium of the injured nerve (typically, about 6-7 millimeters from the distal end), drawing the needle and thread through the interior of distal nerve end 22 into the interior of proximal nerve end 20, and withdrawing the needle and thread at site 24 of the peineurium of the injured nerve (typically, about 6-7 millimeters from the proximal end).

Once the monosuture is in place, tension can be applied to the ends of the monosuture so as to bring nerve ends 20 and 22 into close proximity, preferably within about 0.5 millimeters of each other or even so that the nerve ends are in contact with each other. The suture ends are then tied at sites 24 and 26 to form knots 30 and 32, respectively. Additionally, a piece of connective tissue 34 and 36 may be used at each suture knot to act as a pad and relieve tension between the knot and the perineurium of the nerve. Hence, monosuture 28 serves to coapt the proximal and distal nerve ends 20 and 22 so that there is an extremely small gap between the two nerve ends 20 and 22.

Although it is presently preferable to use a monosuture 28 in connection with prosthesis 10, it will be appreciated that the prosthesis of the present invention may be used without such a monosuture or that other techniques for bringing the nerve ends into close proximity may be used. The reason that it has been found preferable to use a monosuture with the prosthesis of the present invention is that the monosuture places the nerve ends in close proximity while the prosthesis is placed into position; moreover, the monosuture continues to serve to helpmaintain the nerve ends in such close proximity after the prosthesis has been placed into position.

Although the tubular nerve prosthesis may be constructed of any desirable length, for this and many other applications of the present nvention, it is generally desirable to construct the nerve prosthesis of sufficient length that the prosthesis will extend at least about 5-6 millimeters over the proximal end 20 and at least about 2-4 millimeters over the distal end 22 of the severed nerve.

The slit 16 in the tubular prosthesis facilitates its insertion around nerve ends 20 and 22. The thick resilient walls of the prosthesis retract to form a firm seal and to effectively retain fluids within the prosthesis. Since the nerve ends 20 and 22 have a tendency to swell within the thick-walled tubular prosthesis, this swelling coupled with the adherence of the nerve ends 20 and 22 to the preferably textured inner surface of the prosthesis and the renitency of the prosthesis will aid in forming a tight seal between prosthesis 10 and nerve ends 20 and 22.

In this regard, it should be noted that for purposes of the present invention, the most important area for forming such a tight seal is around proximal end 20 of the severed nerve. This is because it is from proximal end 20 that the regenerating units begin to grow. Thus, by securing tubular prosthesis 10 firmly around the nerve ends 20 and 22, and particularly around proximal end 20, the regenerating units are directed directly towards distal end 22 and the trophic substances emanating from proximal end 20 and distal end 22 are prevented from spreading into areas outside of the injured nerve. This serves not only to promote regeneration of the injured nerve, but also to inhibit the formation of a neuroma by controlling the growth and direction of the regenerating units and trophic substances.

As shown in FIG. 2, the monosuture may be used to coapt and secure the injured nerve ends in close proximity. However, when the monosuture is used, it is preferable to apply the terminal knots of the monosuture far away from severed nerve ends 20 and 22 so as to minimize the undesirable effects which would occur, for example, if the very nerve ends themselves were sutured together. As will be appreciated, there are means other than the monosuture which may be used to maintain nerve ends 20 and 22 in close proximity. One such means will be discussed in more detail hereinafter with respect to FIG. 3.

As an optional step in the procedure of applying prosthesis 10 to the first type of nerve injury illustrated in FIG. 2, it may be desirable to remove portions of the epineurial tissue around the area of the severed nerve to which the prosthesis is applied. The epineurial tissue consists of filaments of collagen, and hence, it is sometimes difficult to form a tight seal around the severed nerve ends using prosthesis 10 where there is much epineurial tissue. By trimming away the epineurial tissue, a tighter seal is provided, and the chance of axons escaping in a misrouted direction through the epineurial tissue is minimized. This procedure may also be used in other applications of the present invention.

Another optional procedure which may be used in connection with the placement of a nerve prosthesis within the scope of the present invention involves a small, localized crush of the proximal and distal nerve ends before positioning them within the tubular prostheses. By applying a small localized crush to the severed nerve ends at a point located about 1-2 centimeters from the point of severance, most of the axoplasmic oozing from the proximal and distal nerve ends is stopped. It has been found desirable to stop the oozing of the axoplasm from the nerve ends so that the nerve ends can be cleanly coapted without interference by the axoplasm. Following such a crush to the nerve ends, less edema and axoplasm is present in the gap at the time the regenerating axons reach the gap between the nerve ends. Since edema and axoplasma tend to cause the regenerating axons to be misrouted, minimizing the presence of edema and axoplasma in the gap is desirable.

Such a crushing procedure also serves to delay the arrival of the regenerating axons out of the proximal end of the severed nerve. Hence, since the gap is relatively free and clear of edema and axoplasma by the time the regenerating axons reach the gap between the proximal and distal nerve ends, there is a smaller chance that the regenerating axons will be misrouted and that a neuroma will result.

Although this crushing procedure results in the development of fewer regenerating axons, the axons which are produced are typically larger and do not tend to divide into smaller axons as much as those axons which have not first been crushed. Hence, with fewer and more rapidly regenerating axons, the larger axons have a better chance of bridging the gap between the severed nerve ends and in achieving successful regeneration of the nerve.

It is further believed that the crushing procedure allows the proliferating Schwann cells to migrate out into the gap between the severed nerve ends before the regenerating axons reach this gap. Thus, the gap may be bridged with Schwann cells before the transected axons reach the gap.

If some of the axons start regenerating immediately, as is the case when the nerve ends are not crushed, upon reaching the gap, they grow in a random fashion (in the absence of Schwann cells) and may escape into the epineurium. Conversely, when the Schwann cells have a chance to spread into the gap between the severed nerve ends before the arrival of the regenerating units, they encourage the axon growth in a path towards the distal end of the nerve and also reduce the chances of a neuroma.

It will be appreciated that the optional procedures discussed hereinabove for removing epineurial tissue around the area of the severed nerve ends and for crushing the severed nerve ends at a point located about 1–2 cm from the point of severance, apply not only to the placement of a nerve prosthesis in accordane with the embodiment of FIG. 2, but also to the placement of nerve prosthesis in accordance with the embodiments of FIG. 3, FIG. 4, and FIG. 5 discussed herein, as well as other embodiments of the present invention.

Figure 3:
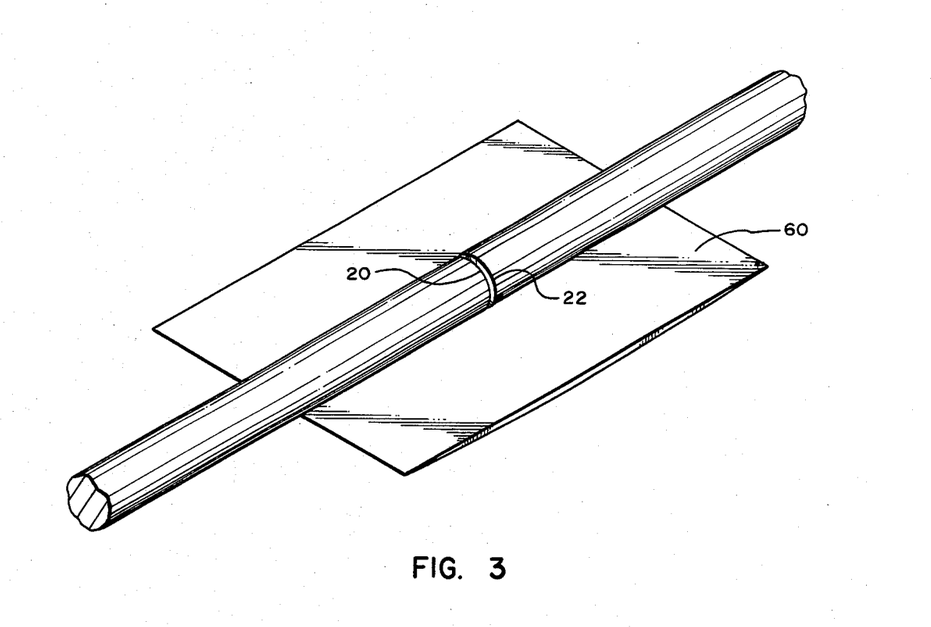
FIG. 3 is a perspective view of another preferred embodiment of a tubular prosthesis within the scope of the present invention as used to treat a nerve injury where there is only a very small gap (or no gap) between the injured nerve ends.

Referring now to FIG. 3, an illustration of a second preferred embodiment of the present invention is shown as it is used to treat a nerve injury where there is only a very small gap (or no gap) between the injured nerve ends. As will be appreciated, this second preferred embodiment may or may not use a monosuture to bring the severed nerve ends together within the prosthesis.

In this second preferred embodiment of FIG. 3, proximal end 20 and distal end 22 are first painted or coated with a fast drying biocompatible polymer, such as nitrocellulose. Ends 20 and 22 are then positioned in close proximity to each other, preferably within at least about 0.5 millimeters, as with the embodiment of FIG. 2. However, in this second preferred embodiment, the prosthesis is formed from a flat sheet of material 60. Nitrocellulose has been found to work well as a material for flat sheet 60 in this second preferred embodiment; nitrocellulose is commercially available and is sold, for example, under the tradename Parlodian.

Nitrocellulose sheet 60 is drawn around the nerve ends 20 and 22 and the edges of the nitrocellulose material 60 are solvent welded together, for example with ether, so as to form a tubular prosthesis around the severed nerve ends. When sheet 60 is so formed, the resultant prosthesis has the same general tubular configuration as prosthesis 10 in FIGS. 1 and 2, but need not be as thick as prosthesis 10 of FIGS. 1 and 2 and will not have rounded ends. Moreover, there will be a ridge in the prosthesis formed from sheet 60 where the edges of the sheet are solvent welded together.

In the embodiment of FIG. 3, it is generally desirable to paint nerve ends 20 and 22 with nitrocellulose so that a tight seal will be formed between the nerve ends 20 and 22 and the tubular prosthesis formed from sheet 60. Since nitrocellulose adheres well to the collagen in the epineurium of the severed nerve, nitrocellulose is the preferred material for the prosthesis of FIG. 3. Additionally, as nitrocellulose dries, it shrinks; thus an even tighter seal with the severed nerve is formed with the nitrocellulose prosthesis of FIG. 3. However, it will be appreciated that other materials may also adhere well to the epineurium of the severed nerve and may also be used in accordance with the present invention.

From the foregoing, it will be appreciated that sheet 60 which forms the prosthesis in the embodiment of FIG. 3 need not be constructed of resilient or renitent material as is the case with the embodiment of FIG. 2, since this prosthesis does not relay upon the wall properties of resiliency and renitency to form a firm seal around the injured nerve ends. Rather, in the embodiment of FIG. 3, the firm seal is formed by tightly wrapping sheet 60 around the nerve ends 20 and 22 to form a tight seal in accordance with the present invention, and further, by adherence of the painted nerve ends 20 and 22 to sheet 60. Hence, it will be appreciated that the prosthesis of FIG. 3 need not be constructed of material as thick as the material forming the prosthesis embodiment of FIG. 2.

Figure 4:
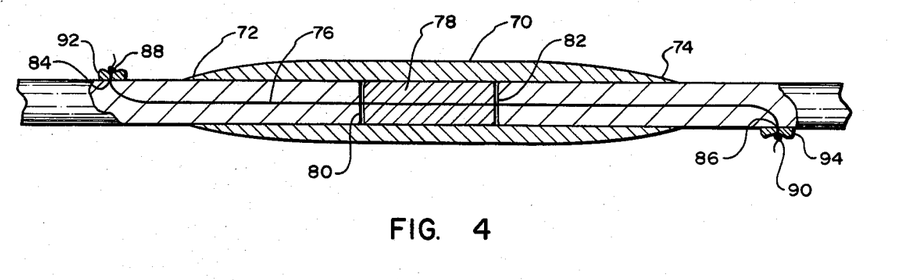
FIG. 4 is a longitudinal cut-away, cross-sectionnal view of a tubular prosthesis within the scope of the present invention as used to treat a nerve injury where there is a gap of one to two centimeters or more between the severed nerve ends.

Referring now to FIG. 4, the application of the present invention to a second type of nerve injury is illustrated. In this second type of injury, more substantial injury to the nerve has occurred such that there is a one to two centimeter (or larger) gap between the severed nerve ends. Because of the larger gap, the tubular prosthesis used, designated 70 in FIG. 4, is, of course, somewhat longer than the tubular prosthesis used to bridge short gaps.

As illustrated in FIG. 4, tubular prosthesis 70 has rounded ends 72 and 74 similar to the ends of prosthesis 10 of FIGS. 1 and 2. Additionally, a monosuture 76 may also be used with this embodiment. Thus, the primary difference between tubular prosthesis 70 used in FIG. 4 and prosthesis 10 used in FIG. 2, besides the obvious difference in length, is that an animal nerve graft 78 is incorporated into prosthesis 70. Thus, as illustrated in FIG. 4, the tubular prosthesis acts as a perineurial homologue, while the animal nerve graft acts as an endoneurial homologue.

The purpose of the animal nerve graft 78 is to provide a scaffold for the regenerating units as they grow from proximal end 80 towards distal end 82 of the severed nerve. This nerve graft may be derived from any suitable source, such as bovine or rabbit sources.

An important feature of the present invention is to remove histocompatibility factors from the animal nerve graft so as to minimize the potential of rejection of the nerve graft by the body of the host, and yet retain the important structural features of the animal nerve graft to provide a scaffold for the regenerating nerve.

A procedure for preparing the nerve graft according to the presently preferred procedure of the present invention is as follows. First, the animal nerve graft is placed in fresh deionized water every two hours for a period of about eight to twelve hours. The absence of osmotic substances in deionized water serves to swell and rupture cells in the nerve graft, and thus to remove the cytoplasm bound by these cells as well as the proteins in the cell membranes of the nerve graft which include histocompatibility factors.

After treatment by the deionized water, the following structural features of the animal nerve graft preferably and desirably remain intact: (1) the basal lamina of the endioneurial tube, (2) the lipid components of cell membranes, and (3) the collagen of the epineurium and endoneurium. It is important that the basal lamina be left intact since it is the basal lamina which attracts Schwann cells, and as discussed above, Schwann cells are essential to proper nerve regeneration.

After treatment with the deionized water, the nerve graft is lyophilized (freeze-dried) to maintain its shape. Additionally, by drying the nerve graft in this manner, the graft has a tendency to attract the trophic substances from the proximal and distal ends of the severed nerve when used within a tubular prosthesis in accordance with the present invention.

After treatment with the deionized water, the nerve graft may be immersed into an aqueous solution of nerve regeneration promoting substances, such as nerve growth factor. (Nerve growth factor may be obtained, for example, from male mouse saliva, by procedures well-known in the art.) The nerve graft is then again dried by lyophilization.

Subsequently, the nerve graft is preferably sterilized by any well-known technique, such as gamma radiation or sterilizing gas, e.g., ethylene oxide. Finally, the ends of the nerve graft are cut so as to provide even ends, and the nerve graft is ready for incorporation into the nerve prosthesis 70.

To achieve implantation in this second type of nerve injury, the injury nerve ends are secured within the prosthesis much in the same way as when there is a very small gap between the severed nerve ends. Prosthesis 70 is opened along its longitudinal slit, and nerve graft 78, as well as nerve ends 80 and 82, are placed within the interior of prosthesis 70 as shown in FIG. 4, such that nerve ends 80 and 82 are in close proximity to the ends of nerve graft 78. Preferably, proximal end 80 is brought to within at least about 0.5 millimeters from one end of nerve graft 78, while distal end 82 is preferably brought to within at least about 0.5 millimeters from the other end of nerve graft 78 within prosthesis 70.

A monosuture 76 may be used to secure nerve ends 80 and 82 in such close proximity with the ends of nerve graft 78. Monosutre 76 is formed much in the same way as monosuture 28 of the embodiment of FIG. 2, however, a longer needle is needed in order to situate monostructure 76. Thus, the needle and monostructure 76 are inserted through the perineurium at site 86 of the injured nerve and are introduced through the endoneurium of distal end 82, thence through animal nerve graft 78, into proximal nerve end 80, and finally through site 84 of the perineurium of the injured nerve. Monosuture 76 is tied to form knots 88 and 90 at sites 84 and 86, respectively, and optionally, a pad of connective tissue 92 and 94, respectively, may be used to cushion each knot against the surface of the injured nerve.

Prosthesis 70 is then tightly secured around the injured nerve in substantially the same fashion as with the embodiment illustrated in FIG. 2, i.e., by allowing the thick-walled, resilient, yet renitent, prosthesis 70 to return to its closed position. However, as with the embodiment of the present invention illustrated in FIG. 2, nerve prosthesis 70 of FIG. 4 may be secured to the injured nerve by other means.

Moreover, prosthesis 70 of FIG. 4 may be secured to the injured nerve by forming the prosthesis in a fashion similarly to the embodiment set forth in FIG. 3. This is done by forming the tubular prosthesis from a sheet of material, for example, nitrocellulose, and wrapping the nitrocellulose sheet around both the nerve graft 78 and the nerve ends 80 and 82 to form the tubular prosthesis. The edges of the prosthesis may then be solvent sealed with ether, as explained previously with respect to the embodiment of FIG. 3. As with the embodiment of FIG. 3, nerve ends 80 and 82 should be painted with nitrocellulose so as to achieve proper adherence of nerve ends 80 and 82 to the nitrocellulose sheet which forms the tubular prosthesis.

Figure 5:
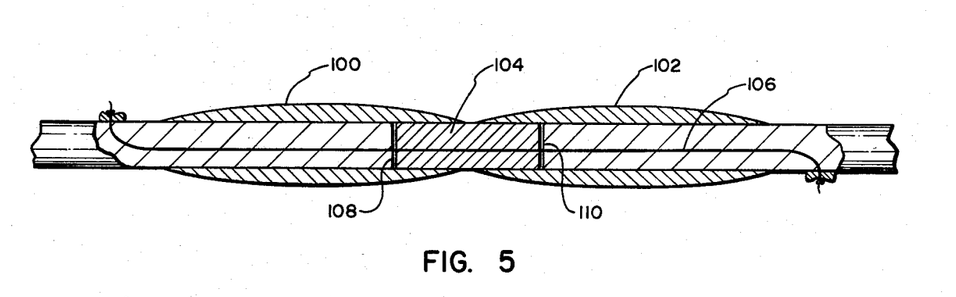
FIG. 5 is a longitudinal cut-away, cross-sectional view of a plurality of tubular prostheses within the scope of the present invention as used to treat a nerve injury where there is a gap of one to two centimeters or more between the severed nerve ends.

Referring now to FIG. 5, a second embodiment of the application of the present invention to the second type of nerve injury is illustrated. The primary difference between the second embodiment of FIG. 5 and the first embodiment of FIG. 4 is that in the embodiment of FIG. 5, two prostheses are used instead of one.

Thus, in this second embodiment of FIG. 5, two tubular prothesis 100 and 102, similar in construction to prosthesis 10 of FIG. 1, are employed in conjunction with an animal nerve graft 104. Alternatively, prosthesis 100 and 102 could be constructed according to the embodiment of FIG. 3.

Animal nerve graft 104 is prepared in identical fashion to animal nerve graft 78 of FIG. 4. Each end of nerve graft 104 is then enclosed within either tubular prosthesis 100 or 102 as illustrated in FIG. 5, and the injured nerve ends 108 and 110 are enclosed within the prostheses in the same fashion as the first embodiment of FIG. 4.

Proximal end 108 of the severed nerve is situated in prosthesis 100 so as to be in close proximity with one end of animal nerve graft 104, while distal end 110 of the severed nerve is situated in prosthesis 102 such that distal end 110 is in close proximity with the other end of the animal nerve graft. A monosuture 106 is used to bring and hold nerve ends 108 and 110 into close proximity with the ends of nerve graft 104, much in the same manner as with the embodiment of FIG. 4. Prostheses 100 and 102 are then secured to injured nerve ends 108 and 110 and nerve graft 104 by firm closure of prostheses 100 and 102.

In treating a nerve injury where there is a large gap, it may be desirable to impregnage the animal nerve graft with one or more nerve regeneration promoting substances to further encourage regeneration of the nerve tissue across the gap.

Some nerve regeneration promoting substances which have been found to be useful for purposes of the present invention include fibronectin, angiogenesis factors, nerve growth factor, extracts of mature and immature central nervous tissue, e.g., central nervous system homogenate, and Schwann cells and the products of Schwann cell cultures. These nerve regeneration promoting substances are introduced directly into the animal nerve graft which is to be situated inside of the tubular nerve prosthesis.

The tubular nerve prostheses of the present invention may be used to promote regeneration of groups of funiculi or to regerate individual funiculi, as desired. If the nerve is small, it may be desirable to use the prosthesis to unite the entire nerve. If the nerve is large, it may be desirable to use several prostheses to unite individual funiculi or groups of small funiculi.

The tubular nerve prostheses of the present invention provide a means for bringing the proximal and distal nerve ends together without actually suturing the nerve ends together using multiple microsutures. Thus, the present invention avoids the problems of the prior art wherein the regenerating axons are misrouted by suturing the very nerve ends together so as to place tension on the nerve ends and complicate the gap area between the nerve ends, thereby increasing the chances of neuroma formation. Moreover, the tubular nerve prostheses of the present invention serve to guide the regenerating units toward the distal end of the nerve within a tightly fitting tube so as to promote regeneration of the nerve tissue and at the same time prevent growth of the regenerating axons in other directions so as to prevent the formation of a neuroma.

Additionally, the impermeable nature of the tubular nerve prostheses of the present invention serves to keep trophic substances within the prosthesis so as to further promote nerve regeneration and inhibit misdirected growth of the the regenerating axons. The impermeability of the prosthesis also serves to isolate the animal nerve graft, when incorporated into the prosthesis, from the rest of the body of the host. This substantially minimizes the chance of an immune response by the body resulting in rejection of the nerve graft.

The tight fitting nature of the tubular nerve prostheses of the present invention also serves to maintain the trophic substances within the prosthesis and to isolate the nerve regeneration process from the rest of the body of the host. Finally, the tubular nerve prosthesis and monosuture provide structural support for keeping the nerve ends positioned closely together or in close proximity with the animal nerve graft, while avoiding the disadvantages of the prior art technique of suturing the nerve ends directly together using multiple microsutures.

The present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of promoting nerve repair, comprising the steps of:
    providing a resilient yet renitent prosthesis which is substantially impermeable to fluids associated with nerve tissue, the impermeable prosthesis serving to substantially prevent the escape of trophic substances through the prosthesis and to substantially prevent the misrouting of regenerating axons out of the prosthesis upon installation of the prosthesis, thereby substantially preventing the formation of a neuroma;
    forming a longitudinal slit along the prosthesis so as to form two longitudinal edges which abut so as to substantially prevent the escape of trophic substances along the slit when the longitudinal edges are in the closed position;
    opening the longitudinal edges of the prosthesis;
    inserting a proximal end of a severed nerve in a first end of the prosthesis;
    inserting a distal end of the severed nerve in a second end of the prosthesis;
    bringing the proximal end of the severed nerve into close proximity with the distal end of the severed nerve; and
    allowing the prosthesis to close around the severed nerve such that the prosthesis forms a close, fluid-tight seal around the proximal end of the severed nerve so as to substantially prevent trophic substances within the prosthesis from escaping out of the prosthesis.

2. A method as defined in claim 1 wherein the prosthesis serves to maintain the proximal end of the nerve within at least about 0.5 millimeters from the distal end of the severed nerve.

3. A method as defined in claim 1 wherein the first end of the prosthesis extends over the proximal end of the severed nerve by at least about 5 millimeters.

4. A method as defined in claim 1 wherein the second end of the prosthesis extends over the distal end of the severed nerve by at least about 2 millimeters.

5. A method as defined in claim 1 further comprising the step of maintaining the proximal end of the severed nerve in close proximity with the distal end of the severed nerve without suturing the nerve ends together.

6. A method as defined in claim 1 further comprising the step of using a monosuture to maintain the proximal end of the severed nerve in close proximity with the distal end of the severed nerve.

7. A method as defined in claim 1 further comprising the step of applying a localized crush along the proximal nerve end at a point located at about 1–2 centimeters from the point of severance before enclosing the nerve ends in the prosthesis.

8. A method as defined in claim 1 wherein the thickness of the wall of the prosthesis is in the range of from about 30% to about 50% of the inner diameter of the prosthesis, the wall of the prosthesis being resilient yet renitent.

9. A method of promoting nerve repair, comprising the steps of:
    providing a resilient yet renitent tube which is biocompatible and which is substantially impermeable to fluids associated with nerve tissue, the impermeable tube serving to substantially prevent the escape of trophic substances through the tube and to substantially prevent the misrouting of regenerating axons out of the tube upon installation of the tube, thereby substantially preventing the formation of a neuroma;
    forming a longitudinal slit along the length of the tube so as to form two longitudinal edges which abut so as to substantially prevent the escape of trophic substances along the slit when the longitudinal edges are in the closed position;
    opening the longitudinal edges of the tube;
    inserting a proximal end of a severed nerve through the slit into a first end of the tube;
    inserting a distal end of the severed nerve through the slit into a second end of the tube;
    positioning the proximal end of the severed nerve within at least about 0.5 millimeters from the distal end of the severed nerve;
    using a monosuture to maintain the proximal end of the severed nerve in close proximity with the distal end of the severed nerve; and
    allowing the tube to close around the severed nerve such that the tube forms a close, fluid-tight seal around the proximal end and the distal end of the severed nerve so as to substantially prevent trophic substances within the tube from escaping out of the tube.

10. A method as defined in claim 9 further comprising the step of:
applying a localized crush along the proximal nerve end at a point located at about 1-2 centimeters from the point of severance before enclosing the nerve ends in the tube.

11. a method of promoting nerve repair, comprising the steps of:
providing a resilient yet renitent tube which is substantially impermeable to fluids associated with nerve tissue, the impermeable tude serving to substantially prevent the escape of trophic substances through the tube and to substantially prevent the misrouting of regenerating axons out of the tube upon installation of the tube, thereby substantially preventing the formation of a neuroma;
forming a longitudinal slit along the length of the tube so as to form two longitudinal edges which abut so as to subtantially prevent the escape of trophic substances along the slit when the longitudinal edges are in the closed position;
opening the longitudinal edges of the tube;
positioning a nerve graft within the tube;
inserting a proximal end of a severed nerve through the slit into a first end of the tube such that the proximal end is positioned in close proximity to a first end of the nerve graft;
inserting a distal end of the severed nerve through the slit into a second end of the tube such that the distal end is positioned in close proximity to a second end of the nerve graft;
forming a monosuture to maintain the proximal end of the severed nerve in close proximity to the first end of the nerve graft and to maintain the distal end of the severed nerve in close proximity to the second end of the nerve graft; and
allowing the tube to close around the severed nerve and the nerve graft such that the tube forms a close, fluid-tight seal around the proximal end of the severed nerve so as to substantially prevent trophic substances within the tube from escaping out of the tube.

12. A method as defined in claim 11 further comprising the step of securing the tube closely around the second end of the nerve graft.

13. A method as defined in claim 11 further comprising the step of treating the nerve graft with deionized water to remove histocompatibility factors prior to positioning the nerve graft within the tube.

14. A method as defined in claim 11 wherein the nerve graft is obtained from a bovine source.

15. A method as defined in claim 11 wherein the nerve graft is obtained from a rabbit.

16. A method as defined in claim 11 further comprising the step of filling the nerve graft with a nerve regeneration promoting substance.

17. A method as defined in claim 16 wherein the nerve regeneration promoting substance comprises fibronectin.

18. A method as defined in claim 16 wherein the nerve regeneration promoting substance comprises an angiogenesis factor.

19. A method as defined in claim 16 wherein the nerve regeneration promoting substance comprises nerve growth factor.

20. A method as defined in claim 16 wherein the nerve regeneration promoting substance comprises central nervous system tissue.

21. A method as defined in claim 16 wherein the nerve regeneration promoting substance comprises Schwann cells.

22. A method as defined in claim 11 wherein the tube serves to maintain the proximal end of the severed nerve within at least about 0.5 millimeters from the first end of the nerve graft and to maintain the distal end of the severed nerve within at least about 0.5 millimeters from the second end of the nerve graft.

23. A method as defined in claim 11 wherein the first end of the tube extends over the proximal end of the severed nerve by at least about 5 millimeters.

24. A method as defined in claim 11 wherein the second end of the tube extends over the distal end of the severed nerve by at least about 2 millimeters.

25. A method as defined in claim 11 further comprising the step of maintaining the proximal end of the severed nerve in close proximity with the first end of the nerve graft and maintaining the distal end of the severed nerve in close proximity with the second end of the nerve graft without suturing the severed nerve ends to the nerve graft.

26. A method of promoting nerve regeneration, comprising the steps of:
providing a resilient yet renitent tube which is biocompatible and which is substantially impermeable to fluids associated with nerve tissue, the impermeable tube serving to substantially prevent the escape of trophic substances through the tube and to substantially prevent the misrouting of regenerating axons out of the tube upon installation of the tube, thereby substantially preventing the formation of a neuroma;
forming a longitudinal slit along the length of the tube so as to form two longitudinal edges which abut so as to substantially prevent the escape of trophic substances along the slit when the longitudinally edges are in the closed position;
opening the longitudinal edges of the tube;
positioning a nerve graft within the tube;
filling the nerve graft with a nerve regeneration promoting substance;
inserting a proximal end of a severed nerve through the slit into a first end of the tube such that the proximal end is positioned within at least about 0.5 millimeters from a first end of the nerve graft;
inserting a distal end of the severed nerve through the slit into a second end of the tube such that the distal end is positioned within at least about 0.5 millimeters away from a second end of the nerve graft;
forming a monosuture to maintain the proximal end of the severed nerve in close proximity to the first end of the nerve graft and to maintain the distal end of the severed nerve in close proximity to the second end of the nerve graft; and
allowing the tube to close around the severed nerve and the nerve graft such that the tube forms a close, fluid-tight seal around the proximal end and the distal end of the severed nerve and such that the tube forms a close, fluid-tight seal around the first end and the second end of the nerve graft so as to substantially prevent trophic substances within the tube from escaping out of the tube.

27. A method as defined in claim 26 further comprising the step of:
applying a localized crush along the proximal nerve end at a point located at about 1-2 centimeters from the point of severance before inserting the nerve ends into the tube.

* * * * *

UNITED STATES PATENT AND TRADEMARK OFFICE
CERTIFICATE OF CORRECTION

PATENT NO. : 4,662,884

DATED : May 5, 1987

INVENTOR(S) : Larry J. Stensaas et al.

It is certified that error appears in the above-identified patent and that said Letters Patent is hereby corrected as shown below:

Column 1, line 24, "nultiple" should be --multiple--
Column 2, line 13, "endoneuril" should be --endoneurial--
Column 4, line 6, "actual" should be --actually--
Column 4, line 13, "laer" should be --layer--
Column 4, line 48, "degeneating" should be --degenerating--
Column 4, line 52, "substantes" should be --substances--
Column 4, line 68, "is regenerating" should be --of regenerating--
Column 5, line 60, "casues" should be --causes--
Column 6, lines 53-54, "presention invention" should be --present invention--
Column 7, line 35, "preferably" should be --preferable--
Column 7, lines 42-43, "the material to material." should be --material to material.--
Column 9, line 52, "helpmaintain" should be --help maintain--
Column 12, line 18, "relay" should be --rely--
Column 13, line 34, "injury" should be --injured--
Column 15, line 1, "tubularnerve" should be --tubular nerve--
Column 17, line 11, "a. method" should be --A method--
Column 18, line 37, "when the longitudinally" should be --when the longitudinal--

Signed and Sealed this

Twenty-fourth Day of November, 1987

Attest:

DONALD J. QUIGG

Attesting Officer      Commissioner of Patents and Trademarks